(12) United States Patent
Gründig et al.

(10) Patent No.: US 6,569,304 B1
(45) Date of Patent: May 27, 2003

(54) PLANAR OPEN REFERENCE ELECTRODE FOR USE IN VOLTAMMERIC MEASURING CHAINS

(75) Inventors: Bernd Gründig, Leipzig (DE); Holm Kopinke, Leipzig (DE); Sybille Wollermann, Böhlen (DE)

(73) Assignee: SensLab Gesellschaft zur Entwicklung und Herstellung bioelektrochemischer Sensoren mbH, Leipzig (DE)

(*) Notice: Subject to any disclaimer, the term of this patent is extended or adjusted under 35 U.S.C. 154(b) by 0 days.

(21) Appl. No.: 09/547,473

(22) Filed: Apr. 12, 2000

(30) Foreign Application Priority Data

Apr. 13, 1999 (DE) .......................... 199 17 830

(51) Int. Cl.⁷ .............................. G01N 27/30
(52) U.S. Cl. ................. 204/435; 204/418; 205/775
(58) Field of Search ................. 204/415, 416, 204/418, 435; 205/775

(56) References Cited

U.S. PATENT DOCUMENTS

| | | | |
|---|---|---|---|
| 2,338,713 A | * | 1/1944 | Ewing |
| 3,192,144 A | * | 6/1965 | Heuze |
| 3,926,764 A | * | 12/1975 | Ruzicka et al. |
| 4,031,606 A | * | 6/1977 | Szonntagh |
| 4,861,454 A | * | 8/1989 | Ushizawa et al. |
| 4,980,043 A | | 12/1990 | Katsuhiko .............. 204/414 |
| 5,182,005 A | * | 1/1993 | Schwizgk et al. |
| 5,509,410 A | | 4/1996 | Hill |
| 5,736,029 A | | 4/1998 | Pinkowski .............. 205/789 |
| 5,820,551 A | | 10/1998 | Hill .............. 600/347 |
| 5,916,156 A | | 6/1999 | Hildenbrnad .............. 600/347 |

FOREIGN PATENT DOCUMENTS

| | | |
|---|---|---|
| EP | 0304933 | 12/1996 |
| EP | 0776675 | 6/1997 |

OTHER PUBLICATIONS

Hackh's Chemical Dictionary, 4th ed., 1969 month unavailable, p. 519.*

M. Lambrechts et al.; Biosensors: Microelectrochemical Devices; Institute of Physics Publishing, 1992 month unavailable, pp. 156–181.

* cited by examiner

*Primary Examiner*—T. Tung
(74) *Attorney, Agent, or Firm*—Bruce S. Londa; Norris, McLaughlin & Marcus, P.A.

(57) ABSTRACT

The invention relates to reference electrodes for use in voltammetric measuring chains for oxidative as well as reductive detection of analytes, which are open with respect to the measuring medium. A metal-containing phthalocyanine or a metalloporphyrin is employed as potential-determining electrode material for reference electrodes of the invention used in oxidative detection. A fourth period metal, preferably copper, and a salt of said metal is employed as potential-determining electrode material for reference electrodes of the invention used in reductive detection. The potential-determining electrode material is coated as a layer or component of a layer on a planar support. The open reference electrodes according to the invention are particularly suited for voltammetric chemo- or biosensors having a planar structure.

6 Claims, 2 Drawing Sheets

PLANAR OPEN REFERENCE ELECTRODE FOR USE IN VOLTAMMERIC MEASURING CHAINS

BACKGROUND OF THE INVENTION

The invention relates to reference electrodes for use in voltammetric measuring chains for oxidative as well as reductive detection of analytes, which are open with respect to the measuring medium. A metal-containing phthalocyanine or a metalloporphyrin is employed as potential-determining electrode material for reference electrodes of the invention used in oxidative detection. A fourth period metal, preferably copper, and a salt of said metal is employed as potential-determining electrode material for reference electrodes of the invention used in reductive detection. The potential-determining electrode material is coated as a layer or component of a layer on a planar support. The open reference electrodes according to the invention are particularly suited for voltammetric chemo- or biosensors having a planar structure.

When utilizing mass production technologies for voltammetric chemo- and biosensors as known from thin and thick film technologies in microelectronics, problems arise in transferring to planar structures, particularly in case of conventional reference electrodes.

In general, a measuring cell consisting of a measuring or working electrode and a reference electrode, or a potentiostatically working measuring cell consisting of a working electrode, a reference electrode and an auxiliary electrode or counterelectrode is used in the voltammetric detection of analyte concentrations in solution, where the electrodes submerge in the solution to be measured. To ensure a constant reference potential which is required in all types of voltammetric detections in order to adjust a defined working electrode polarization potential, reference electrodes are used that are closed with respect to the measuring medium. A typical example of a voltammetric sensor is the amperometric Clark type oxygen measuring cell which consists of a polarizable working electrode and a non-polarizable reference electrode. When applying a suitable polarization potential between the two electrodes, oxygen will be reduced electro-chemically at the working electrode, thus generating an analyte-proportional depolarization current between the two electrodes in the external circuit. Particularly in the event of current-carrying reference electrodes, care must be taken to have a sufficiently large surface, which must be a multiple of the working electrode surface in order to maintain a constant reference potential. Alternatively, the so-called potentiostate principle is used wherein the reference electrode is virtually free of current load as a result of a suitable electronic control and the use of an additional auxiliary electrode (counterelectrode).

Being electrodes of the second type, a common feature of all traditional reference electrodes for use in aqueous media is to consist of a metal (e.g., mercury or silver), a sparingly soluble compound of said metal, and a phase containing the anion of the metal compound. Consequently, the potential-determining reference electrode material is surrounded by a defined anion concentration of said metal compound and connected with the working electrode via an ionically conducting salt bridge which has a diaphragm at its end.

The salt bridge, normally being filled with chloride concentrations of between 1 M and 3 M, and the diaphragm providing ionic contact with the solution to be measured—in a way that mixing with the salt bridge electrolyte cannot take place—ensure a constant ratio of concentrations of metal/metal salt and metal salt anions and thus, a constant reference potential.

Transferring such a closed reference electrode system to planar structures is only possible with great effort, thus impeding cost-effective mass production. Therefore, voltammetric measuring chains of planar structure, particularly for cost-effective production of voltammetric chemo- and bio-sensors based on thin and thick film technologies, frequently work with open reference electrodes, i.e., in a way that the reference electrode surface is directly exposed to the measuring medium.

Preferably, silver/silver halides are used as metal/metal salt reference electrode system (EP 0,304,933; DE 33 09 251; U.S. Pat. No. 5,509,410). An approximately constant concentration of silver ions is required to maintain the equilibrium potential of a silver reference electrode, which is why silver salts sparingly soluble in water, such as silver chloride, are used. Due to the solubility product, the concentration of silver ions in aqueous media depends substantially on the concentration of chloride ions. Now, when using the silver/silver chloride system without a salt bridge, i.e., with direct exposure to the measuring medium, a number of interferences generally occur, particularly in those cases where measurements have to be performed in undefined media as represented by actual samples. For example, the steady state ionic concentration at the metal/metal salt boundary surface undergoes changes depending on the flow velocity, resulting in a short-term interference of the equilibrium potential and thus, in a potential drift. Moreover, anions of unknown composition and undefined concentration are present in the measuring medium, which in turn produce silver salts and may dominate the reference potential as a result of their solubility product. At least, however, they may give rise to a mixed potential resulting in a more or less substantial potential drift and conceivably, in a high transition resistance Hence, the composition of the ions and their concentration in the measuring medium may have a substantial effect on the reference potential. As described above, an open reference electrode system also is biased by adsorbent substances, metal chelating agents or electrically active substances in the measuring medium and ultimately, by the conditions of diffusion and/or convection at the electrode surface. This situation can largely be compensated by diluting the sample with a defined electrolyte solution and maintaining constant flow conditions.

Under specific conditions, however, particularly as encountered in amperometric biosensors where the biocomponent requires specific buffer materials or ions for a stable and sensitive indication reaction, considerable shifts of the reference potential may occur. For example, when using a phosphate buffer in an open silver/silver chloride reference electrode, silver phosphate will form on the silver electrode despite the presence of chloride ions, giving rise to a reference electrode potential shift by about 150 mV to the negative side. Thus, compared to a closed silver/silver chloride reference electrode, a polarization potential more negative by about 150 mV has to be applied to the working electrode in a reductive indication of an analyte present in its oxidized form, which ultimately also involves an increased susceptibility to interference in the measuring chain with open reference system.

Another aspect of general importance for the oxidative indication of e.g. hydrogen peroxide formed in oxidase-catalyzed reactions relates to the comparatively high polarization potential required in a conventional measuring chain array comprising a platinum working electrode and a silver/ silver chloride reference electrode. While the use of an open measuring chain in phosphate buffer implies a reduction of the polarization potential required, the polarization potential to be applied—still being from +450 mV to +500 mV—involves a considerable risk of interference current effects. Moreover, in case of a quasi-continuous inflow of such an open measuring chain, the transient action of the measuring chain during the transition between resting and flowing medium is expected to proceed slowly as a result of the change in ion concentration and the associated change of the equilibrium potential between metal and metal salt, which in the worst case overlays the generation of measuring values.

Especially in miniaturized potentiometric sensor arrays, attempts were made to adapt the situation of a conventional reference electrode structure in such a fashion that polymeric materials or diaphragms as diffusion barrier layers containing the metal salt anion were coated layer by layer on the reference electrode material (EP 0,247,535; DE 195 33 059; DE 195 34 925), or appropriate reservoirs containing reference electrolyte were provided (Lambrechts, M., Sansen W.: Biosensors: Microelectrochemical devices, Institute of Physics Publishing, Bristol Philadelphia and New York, 1992). In a similar type of construction, planar reference electrodes for amperometric sensors are known (DE 42 41 206; U.S. Pat. No. 4,980,043). Both of these approaches have in common that the layers, diffusion barriers or miniaturized reservoirs ensure not more than limited retaining of the reference electrolyte, and leaking of electrolyte into the measuring medium or diffusion of the solution to be measured to the reference system cannot be prevented over a prolonged period of operation.

The patent specification DE 43 02 322 suggests the use of perchlorate as potential-determining ion in combination with a perchlorate-sensitive diaphragm between the reference electrolyte reservoir and the measuring medium. By using e.g. potassium perchlorate which is introduced in a solid form into the reservoir and has a substantially lower solubility in water than reference electrolytes of second type electrodes, a substantially improved long-term stability is achieved in combination with the perchlorate-sensitive diaphragm. Such a reference system is also useful in potentiostatically operated voltammetric sensors, but—like all the variants including a reservoir—requires a three-dimensional sensor design.

In addition to using a redox reference electrode, another, comparatively expensive solution (DE 43 02 323) suggests a so-called protective electrode within the space of the reference electrolyte, spatially situated between the diaphragm and reference electrode. The potential is measured between the two electrodes. In case of a potential difference at the protective electrode with respect to the reference electrode as a result of inwardly diffusing electrically active substances, a current is generated via an additional counter-electrode in analogy to the potentiostate principle, which reduces or oxidizes the interfering substances until potential parity between protective and reference electrodes is re-established.

In amperometric enzyme sensors, alternative reference electrode materials such as silver/palladium mixtures (U.S. Pat. No. 5,820,551), stainless steel alloys (U.S. Pat. No. 5,736,029) and graphite (EP 0,776,675; U.S. Pat. No. 5,916, 156) have been used in two-electrode systems as pseudo-reference electrodes.

In three-electrode arrays on "open" planar sensor structures operated in so-called potentiostatic operation, silver/silver chloride has essentially been used as reference electrode material until now, involving the problems described above.

SUMMARY OF THE INVENTION

The object of the invention is to provide voltammetric reference electrodes that would avoid the above-mentioned drawbacks and permit less trouble-prone, correct and reproducible measurements. In particular, these electrodes should be cost-effective in production and capable of miniaturization.

Surprisingly, metal-containing phthalocyanines or metalloporphyrins, each present in homogeneous mixture with an inert, conductive material or with an inert, conductive material and a curable binder, were found to be particularly suitable as potential-determining electrode material coated on a planar support and to be used for an open reference electrode of a voltammetric measuring chain, at the working electrode of which an oxidative detection of redox-active analytes takes place. Carbon, e.g. graphite or pyrolytic carbons such as carbon black, or glass-carbon ground to powder, or noble metal powders of gold, platinum or palladium, preferably carbon or a mixture of various types of carbon are used as inert, conductive material. Polymers, preferably poly(vinyl chloride), silicone resins, epoxide resins, phenol resins, acrylates, or mixtures thereof can be used as binders.

DESCRIPTION OF THE PREFERRED EMBODIMENT

Figure 1:
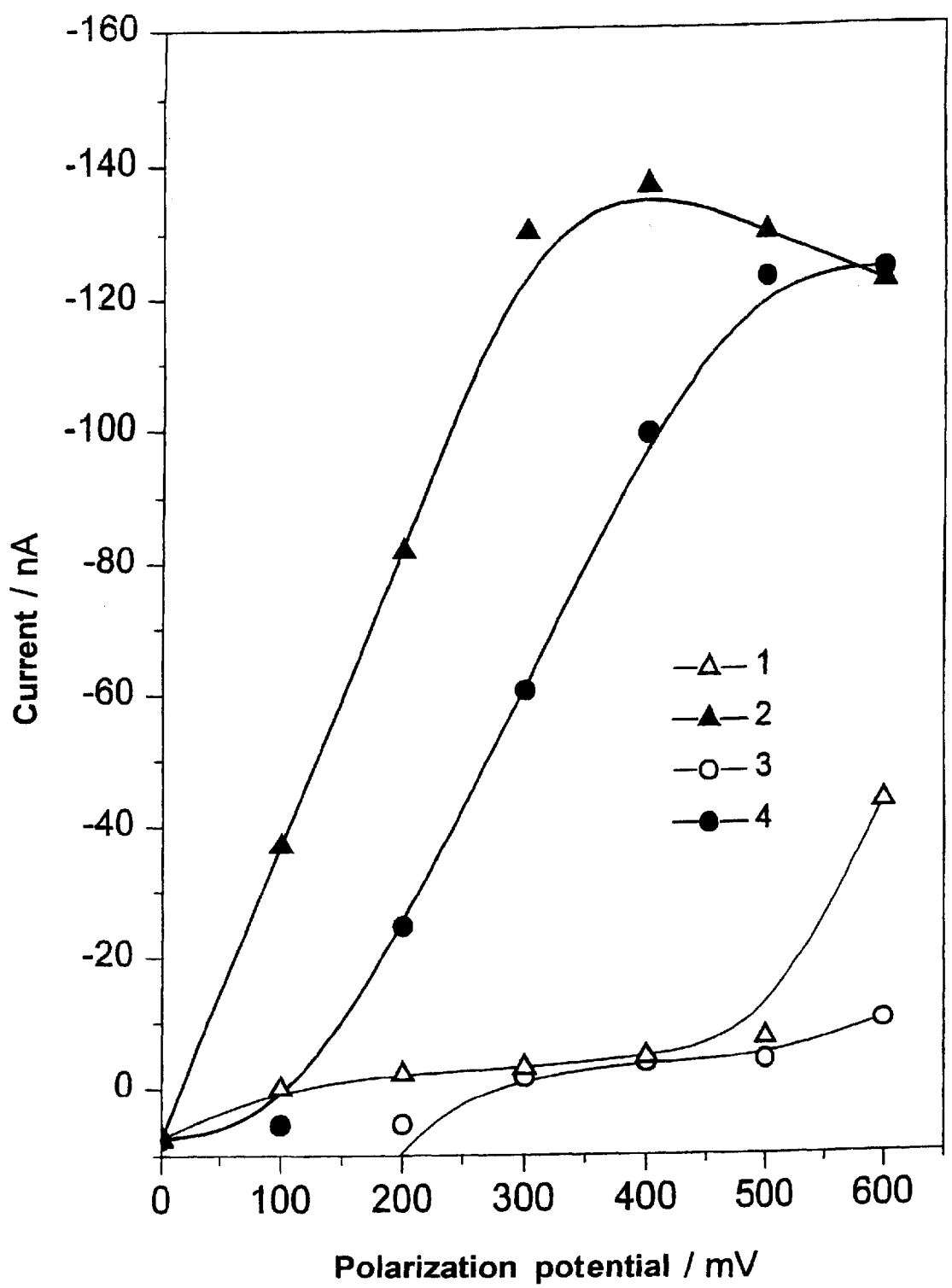
FIG. 1—Graph showing the limited diffusion current plateaus.

In a preferred embodiment of the invention, the reference electrode consists of a planar support coated with a layer containing a powdered phthalocyanine, a type of carbon or a -mixture of various types of carbon, and the polymeric binder in homogeneous dispersion. In particular, the use of metal-containing phthalocyanines as potential-determining reference electrode material, which preferably contain iron, manganese, cobalt, nickel, or copper atoms, reduces the polarization potential required to reach the limiting diffusion current for the oxidation of an analyte to about 150 mV to 200 mV compared to a closed silver/silver chloride reference electrode system.

Ceramic materials, e.g. those based on $Al_2O_3$ or $SiO_2$, or plastic materials such as polyamide, PEEK, polypropylene, fiber-reinforced epoxide and phenol resins or polycarbonates are possible as support materials for the sensors according to the invention, and it is particularly preferred to use polycarbonate as support material.

The open reference electrode for use in voltammetric measuring chains for oxidative detection is produced in such a way that initially, the metal-containing phthalocyanine or metalloporphyrin is mixed homogeneously with the inert material or with the inert material and the curable binder, and the mixture is coated on the support and cured.

Another way of producing is provided by vacuum coating as known from thin layer technology, where the inert, electrically conductive material and the phthalocyanine or metalloporphyrin are coated successively or as a mixture on the support material, optionally using an appropriate mask.

Compared to a silver/silver chloride system used in an open fashion, the electrode material of the invention was found to be essentially less sensitive to variations in the ionic concentration and the composition of the ions in the measuring medium, and it exhibits reduced sensitivity to changes in flow in the measuring medium. As a result, the measurement is less susceptible to interference, has improved correctness and reproducibility (cf., Table 1 in Example 2).

Surprisingly, it has also been found that by using fourth period metals, particularly copper, coated with a salt of an inorganic acid, preferably halogenated, a reference electrode material is provided which is specifically suited for open reference electrodes in a voltammetric measuring chain where the working electrode undergoes reductive polarization. This is so because the polarization potential required to reach the limiting diffusion current for the reduction of an analyte present in its oxidized form is not larger in magnitude than the one involving an external closed silver/silver chloride reference electrode. When using phosphate buffer as a model measuring solution, the required polarization potential is lower in magnitude by 50 mV compared to the external silver/silver chloride reference electrode. Also, the use of a fourth period metal, particularly copper, is advantageous because it is a metal typically used in electronics where well-established thin-layer technological and electroplating processes are available for the processing thereof, and thick layer conductive pastes represent a technological standard. The halogenation, preferably chlorination of a fourth period metal, particularly copper, can be effected both in a chemical and galvanic fashion.

As potential-determining electrode material, the planar open reference electrodes for reductive detection may include the metal and metal salt in homogeneous mixture with an inert conductive material and a curable binder. Carbon, e.g. graphite, pyrolytic carbons such as carbon black, or glass-carbon ground to powder, or noble metal powders of gold, platinum or palladium can be used as inert, conductive material. Preferably, carbon or a mixture of various types of carbon is employed. Preferably, a polymer is possible as curable binder, with poly(vinyl chloride), silicone resins, epoxide resins, phenol resins, acrylates, or mixtures thereof being particularly preferred.

The reference electrodes for reductive detection, open ones according to the invention, the potential-determining electrode material of which merely consisting of a fourth period metal and a salt of said metal, can be produced by coating the metal on the planar support in a well-known manner, e.g. by cathode sputtering or vacuum coating as common in thin layer technology, or by electrochemical deposition on the planar support and subsequent chemical or electrolytical conversion to form a metal salt on the surface.

The reference electrodes of the invention, containing a homogeneous mixture of metal, metal salt, inert material, and curable binder as potential-determining electrode material, are produced from homogeneous mixtures of fourth period metal particles and salts thereof (preferably halogen salts previously produced in a wet-chemical fashion) with the inert, electrically conductive material (such as carbon or a mixture of various types of carbon) and the curable binder. These mixtures are coated on the planar support and cured. Silicon substrates, ceramic materials, e.g. those based on $Al_2O_3$, or plastic materials such as polyamide, PEEK, polypropylene, fiber-reinforced epoxide and phenol resins or polycarbonates can be used as support materials, and it is preferred to use polycarbonates.

Thus, for example, commercially available copper conductive pastes already containing these compounds can be used to produce the electrodes according to the invention having copper and a copper salt as potential-determining electrode material.

In addition to less trouble-prone measurement, the open reference electrodes of the invention for oxidative as well as reductive detection uses in measuring chains of planar structure permit cost-effective and reproducible production by using well-established microelectronics mass production technologies and enable good miniaturizing.

In addition to the reference electrodes and the process for producing same, the invention is also directed to the use of metal-containing phthalocyanines or metallo-porphyrins as potential-determining electrode material for open reference electrodes to be used in voltammetric measuring chains for oxidative detection, and to the use of a fourth period metal and a salt of said metal as potential-determining electrode material for open reference electrodes to be used in voltammetric measuring chains for reductive detection.

EXAMPLE 1

Sensor Including Reference Electrode of the Invention for Oxidative Detection, and Comparative Sensor Using a polymeric silver conductive paste (ESL, GB: D-1120-PG) and a polymeric insulating paste (ESL 242 SB fine line), three silver track conductors and an insulating layer are coated successively on a polycarbonate support material of 60 mm×8 mm so as to produce a measuring window on one side and three connector points for electric contact on the other side. The track conductors with an area of 0.2 $mm^2$ each lead to the measuring window. Following curing of the coated paste layers at 120° C. over 24 hours, a platinum conductive paste (IBH Klingenberg) as working and counterelectrode, having a diameter of 0.5 mm, is coated with a microdispenser in a circular fashion on the surface of each track conductor and cured.

For the reference electrode, cobalt phthalocyanine (Sigma, Deisenhofen, Germany), carbon and epoxide resin are mixed in a ratio of 20:40:40, coated on the third contact point in the measuring window and cured at 90° C. The area of the reference electrode is 0.7 $mm^2$.

A second sensor was produced for comparison which, however, was provided with a silver paste layer (ESL, GB: D-1120-PG) as reference electrode. In order to generate a silver chloride layer, the reference electrode was operated at an anodic voltage of +1 V vs. external Ag/AgCl reference electrode (Metrohm, Filderstadt, Germany) for 1 minute in a 0.1 M HCl solution.

As shown in FIG. 1, the limiting diffusion current plateau in a hydrogen peroxide oxidation for the sensor having the cobalt phthalocyanine/carbon reference electrode system is reached at a polarization potential between +300 mV and +400 mV, while the limiting diffusion current plateau of the sensor having silver/silver chloride as reference electrode system is reached between 500 and 600 mV. The background currents were obtained in a stirred buffer solution, pH 6.8, and the limiting diffusion currents for the oxidation of 0.1 mM hydrogen peroxide were obtained in a stirred buffer solution, pH 6.8.

In FIG. 1, 1 represents the background current of the sensor having the cobalt phthalocyanine/carbon reference electrode material as a function of applied polarization potential; p0 2 represents the limiting diffusion current of the sensor having the cobalt phthalocyanine/carbon reference electrode material as a function of applied polarization potential;

3 represents the background current of the sensor having the silver/silver chloride reference electrode material as a function of applied polarization potential;

4 represents the limiting diffusion current of the sensor having the silver/silver chloride reference electrode material as a function of applied polarization potential.

EXAMPLE 2

Interference Studies on the Sensor of the Invention and the Comparative Sensor of Example 1

Interference studies on the sensor of the invention and the comparative sensor were carried out. The results are illustrated in Table 1.

A comparison of interference studies on the sensor having the open cobalt phthalocyanine/carbon reference system (CoPc/C) and the sensor having the open silver/silver chloride reference system (Ag/AgCl) reveals that the interference currents of the sensor having the cobalt phthalocyanine/carbon reference electrode are significantly lower, i.e., its interference/signal current ratio is more favorable than that of the sensor with silver/silver chloride reference electrode at the appropriate polarization potential required to reach the respective limiting diffusion current of hydrogen peroxide oxidation of the sensors having these different reference electrodes.

TABLE 1

| Reference system | Ag/AgCl | CoPc/C |
|---|---|---|
| Polarization potential (Range of limiting diffusion current) | 500 mV | 300 mV |
| Background current/nA | −4.3 | −2.0 |
| $H_2O_2$ signal current (0.2 mM)/nA | −122.9 | −130.0 |
| Ascorbate interference current (0.1 mM)/nA | −57.7 | −29.0 |
| Paracetamol interference current (0.1 mM)/nA | −51.5 | −43.7 |
| Uric acid interference current (0.1 mM)/nA | −42.6 | −28.6 |
| Interference/signal current ratio: 0.1 mM $H_2O_2$/0.1 mM ascorbate | 0.47 | 0.11 |
| Interference/signal current ratio: 0.1 mM $H_2O_2$/0.1 mM paracetamol | 0.42 | 0.34 |
| Interference/signal current ratio: 0.1 mM $H_2O_2$/0.1 mM uric acid | 0.35 | 0.22 |

EXAMPLE 3

Sensor Including Reference Electrode of the Invention for Reductive Detection, and Comparative Sensor The preparation of the basic sensor, including coating of track conductors and insulating layer, was performed as described in Example 1. A carbon paste (P1, SensLab GmbH, Leipzig, Germany) as working and counterelectrode, having a diameter of 0.5 mm, is coated with a microdispenser in a circular fashion on two of the track conductors in the measuring window and cured. For the reference electrode, a copper conductive paste (CB 200, DuPont, GB) is coated on the third contact point in the measuring window and cured at 110° C. for 16 hours. The area of the reference electrode is 0.7 mm².

When operating the sensor in phosphate buffer, a thin layer of copper phosphate is generated immediately as a result of using the copper reference electrode as anode. For this reason, a previous treatment to form a copper salt is not necessarily required. In case such phosphating is to be effected as early as during preparation, the reference electrode is operated anodically ("electroplated") at a fixed polarization potential of between −200 mV and −800 mV vs. Ag/AgCl for about 30 seconds to 60 seconds in 0.1 M phosphate buffer, pH 6.

A second sensor was produced for comparison which, however, was provided with a silver paste layer (ESL, GB: D-1120-PG) as reference electrode. In order to generate a silver chloride layer, the reference electrode was operated at an anodic voltage of +1 V vs. external Ag/AgCl reference electrode (Metrohm, Filderstadt, Germany) for 1 minute in a 0.1 M HCl solution.

Figure 2:
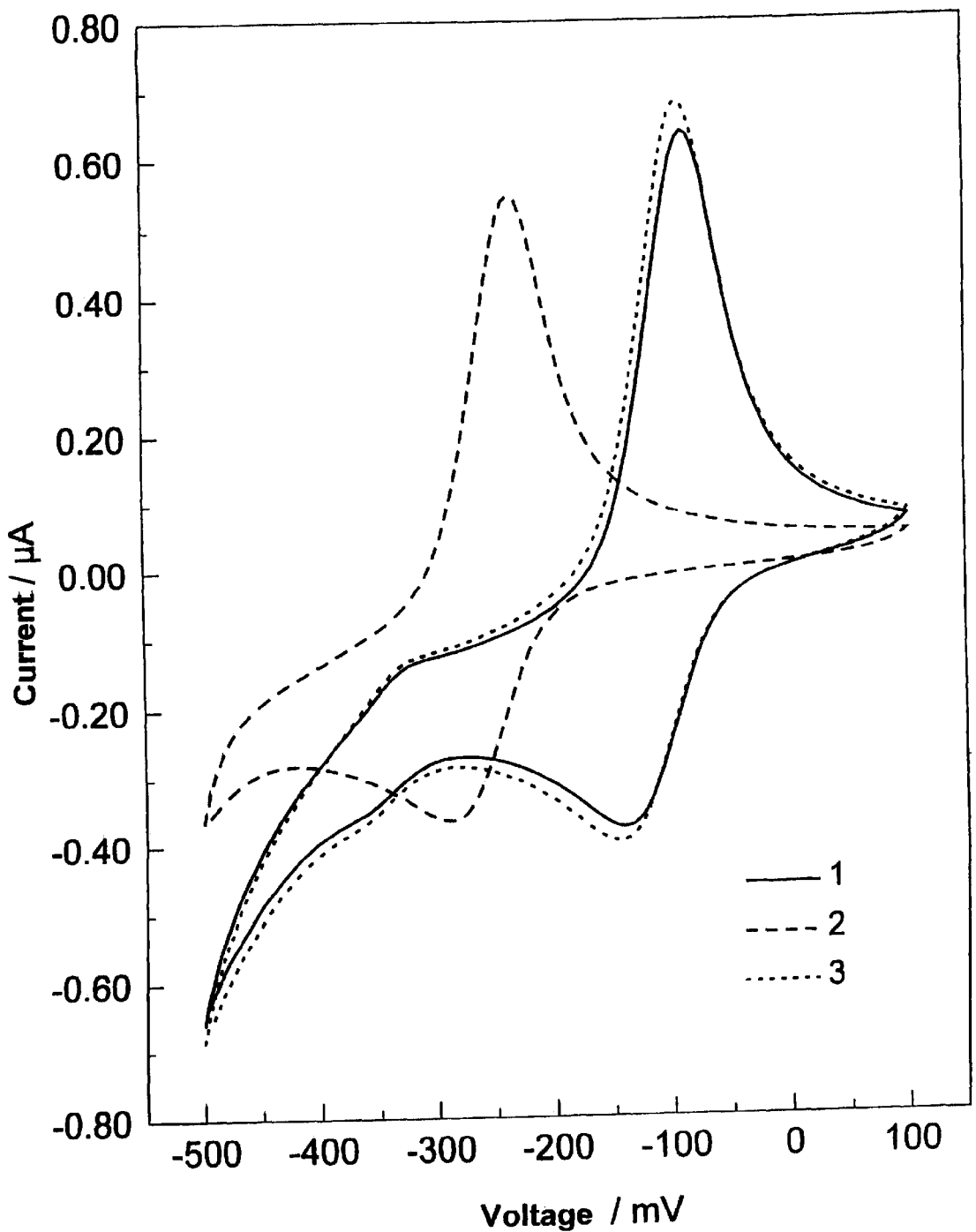
FIG. 2—Graph comparing the open silver/silver chloride reference system and the closed silver/silver choride reference electrode.

As shown in FIG. 2, the open silver/silver chloride reference system—compared to the closed silver/silver chloride reference electrode which is in contact with the solution to be measured via salt bridge and diaphragm—results in a shift in the formal potential of the redox mediator by about 150 mV to the negative side. Compared to an external reference electrode, the formal redox potential of the redox mediator remains virtually unchanged when using the Cu reference system, which is particularly important in the cathodic detection of electrically active substances or enzymatic reaction products.

In FIG. 2, 1 represents a cyclic voltammogram of 0.1 mm 1-methoxyphenazinium methosulfate in phosphate buffer, ph 6.8, at a scan rate of 50 mv/s at a carbon working electrode of a sensor where copper is used as reference system;

2 represents a cyclic voltammogram of 0.1 mm 1-methoxyphenazinium methosulfate in phosphate buffer, ph 6.8, at a scan rate of 50 mv/s at a carbon working electrode of a sensor where silver/silver chloride is used as reference system;

3 represents a cyclic voltammogram of 0.1 mm 1-methoxyphenazinium methosulfate in phosphate buffer, ph 6.8, at a scan rate of 50 mv/s at a carbon working electrode of a sensor where an external silver/silver chloride reference electrode (Metrohm, Filderstadt, Germany) is used as reference system.

What is claimed is:

1. An open reference electrode for use in voltammetric measuring chains for reductive detection of an analyte, consisting of a planar support having a layer coated thereon which comprises a potential-determining electrode material, wherein the potential-determining electrode material consists of copper and a copper halide.

2. The reference electrode according to claim 1, wherein the copper halide is copper chloride.

3. The reference electrode according to claim 1, wherein the layer comprising the potential-determining electrode material includes said copper and copper halide in a homogeneous mixture with an inert, electrically conductive material and a binder.

4. The reference electrode according to claim 3, wherein the inert, electrically-conductive material is carbon or a mixture of various types of carbon.

5. The reference electrode according to claim 3, wherein the binder is a polymer.

6. The reference electrode according to claim 1, wherein the layer comprising the potential-determining electrode material consists of the said copper as the layer having the said copper halide coated on its surface.

* * * * *